(12) United States Patent
Porter et al.

(10) Patent No.: US 8,979,940 B2
(45) Date of Patent: Mar. 17, 2015

(54) MODULAR ATTACHMENT MECHANISM IN PROSTHETIC IMPLANTS

(71) Applicant: Biomet Manufacturing Corporation, Warsaw, IN (US)

(72) Inventors: Joshua R. Porter, Winona Lake, IN (US); Troy W. Hershberger, Winona Lake, IN (US); Aaron P. Smith, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 13/714,570

(22) Filed: Dec. 14, 2012

(65) Prior Publication Data

US 2014/0172115 A1    Jun. 19, 2014

(51) Int. Cl.
*A61F 2/36*    (2006.01)

(52) U.S. Cl.
CPC .................................. *A61F 2/3609* (2013.01)
USPC ..................................................... 623/23.15

(58) Field of Classification Search
USPC .......... 623/18.11, 19.11–19.14, 22.42, 22.11, 623/23.11, 20.35, 22.32, 23.3, 23.22, 23.23, 623/22.36, 22.37, 23.28
See application file for complete search history.

(56) References Cited

U.S. PATENT DOCUMENTS

| | | | | |
|---|---|---|---|---|
| 2,719,522 A * | 10/1955 | Hudack | ...................... | 623/23.15 |
| 4,355,427 A * | 10/1982 | Schneider | .................. | 623/19.14 |
| 4,714,475 A * | 12/1987 | Grundei et al. | ............ | 623/20.32 |
| 4,718,915 A | 1/1988 | Epinette | | |
| 4,988,351 A | 1/1991 | Paulos et al. | | |
| 5,324,291 A * | 6/1994 | Ries et al. | ........................ | 606/71 |
| D368,777 S * | 4/1996 | Goble et al. | .................. | D24/145 |
| D374,286 S * | 10/1996 | Goble et al. | .................. | D24/145 |
| D374,482 S * | 10/1996 | Goble et al. | .................. | D24/145 |
| D375,791 S * | 11/1996 | Goble et al. | .................. | D24/145 |
| 5,658,349 A * | 8/1997 | Brooks et al. | ............... | 623/23.23 |
| 5,665,088 A * | 9/1997 | Gil et al. | ......................... | 606/74 |
| 5,797,916 A * | 8/1998 | McDowell | ...................... | 606/74 |
| 5,944,758 A * | 8/1999 | Mansat et al. | .............. | 623/19.14 |
| 6,066,141 A * | 5/2000 | Dall et al. | ........................ | 606/74 |
| 6,127,596 A * | 10/2000 | Brown et al. | ............... | 623/16.11 |
| 6,283,999 B1 * | 9/2001 | Rockwood, Jr. | ............ | 623/19.12 |
| 6,398,812 B1 * | 6/2002 | Masini | ....................... | 623/19.14 |
| 6,482,232 B1 * | 11/2002 | Boucher et al. | ............ | 623/13.14 |
| 6,520,994 B2 * | 2/2003 | Nogarin | ..................... | 623/19.14 |

(Continued)

FOREIGN PATENT DOCUMENTS

FR    2732891 A1    10/1996

OTHER PUBLICATIONS

"Arcos® Modular Femoral Revision System Surgical Technique" brochure. (Sep. 2010) pp. 1-92.

(Continued)

*Primary Examiner* — Alvin Stewart
(74) *Attorney, Agent, or Firm* — Harness, Dickey

(57) ABSTRACT

Disclosed is an apparatus that can be positioned in a subject to include, selectively, a modular connection portion. The modular connection portion can be provided to allow for soft tissue connection that replaces a greater trochanter of a natural femur. The soft tissue connection portion can include a plurality of regions to allow for reattachment of soft tissue in a plurality of position to mimic a natural anatomy. A method of using, selecting, and implanting the prosthesis is also disclosed.

25 Claims, 10 Drawing Sheets

(56) References Cited

U.S. PATENT DOCUMENTS

| | | | |
|---|---|---|---|
| 6,592,622 B1* | 7/2003 | Ferguson | 623/13.14 |
| 7,070,622 B1* | 7/2006 | Brown et al. | 623/20.14 |
| 7,175,664 B1* | 2/2007 | Lakin | 623/19.14 |
| 7,179,259 B1* | 2/2007 | Gibbs | 606/64 |
| 8,118,868 B2* | 2/2012 | May et al. | 623/13.14 |
| 8,177,849 B2* | 5/2012 | Meyers et al. | 623/20.32 |
| 8,182,542 B2* | 5/2012 | Ferko | 623/19.14 |
| 8,226,725 B2* | 7/2012 | Ferko | 623/20.14 |
| 8,252,061 B2* | 8/2012 | Mikami et al. | 623/23.15 |
| 8,574,235 B2* | 11/2013 | Stone | 606/74 |
| 8,579,984 B2* | 11/2013 | Borowsky | 623/19.14 |
| 2007/0129809 A1* | 6/2007 | Meridew et al. | 623/22.32 |
| 2007/0244565 A1* | 10/2007 | Stchur | 623/19.14 |
| 2008/0021566 A1* | 1/2008 | Peters et al. | 623/20.16 |
| 2008/0133024 A1* | 6/2008 | Meswania | 623/22.42 |
| 2008/0177393 A1* | 7/2008 | Grant et al. | 623/18.11 |
| 2008/0255622 A1* | 10/2008 | Mickiewicz et al. | 606/319 |
| 2008/0281428 A1* | 11/2008 | Meyers et al. | 623/20.35 |
| 2011/0009973 A1* | 1/2011 | Meyers et al. | 623/20.32 |
| 2011/0213467 A1* | 9/2011 | Lozier et al. | 623/20.32 |
| 2011/0218641 A1* | 9/2011 | Smith et al. | 623/22.42 |
| 2012/0010720 A1* | 1/2012 | Dickerson | 623/22.42 |
| 2012/0191202 A1* | 7/2012 | Borowsky | 623/19.11 |
| 2012/0191207 A1* | 7/2012 | Meyers et al. | 623/20.35 |

OTHER PUBLICATIONS

"Segmental Distal Femur," OSS™ Orthopaedic Salvage System brochure. Biomet Orthopedics, Inc. (2003) pp. 1-20.

* cited by examiner

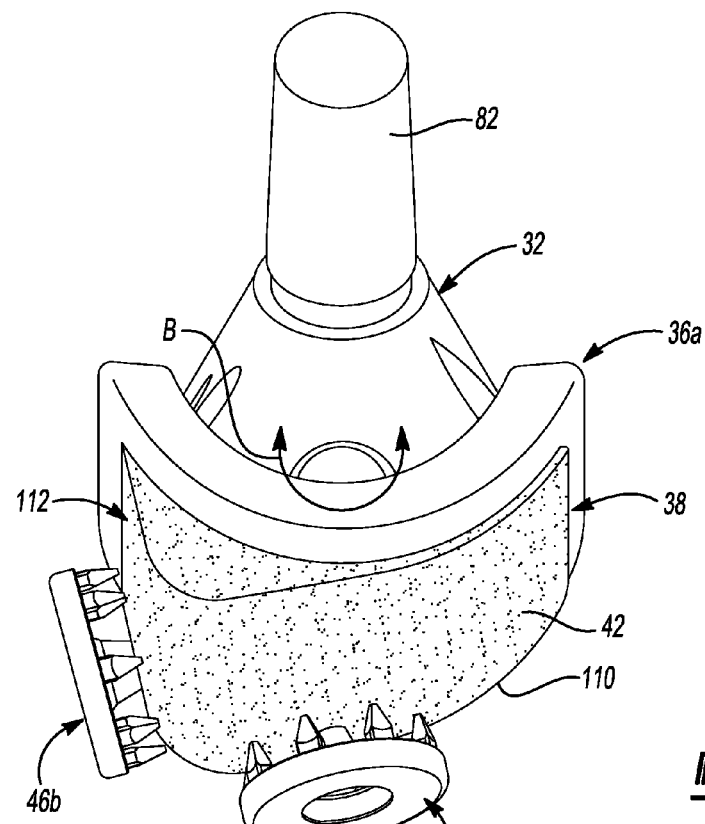
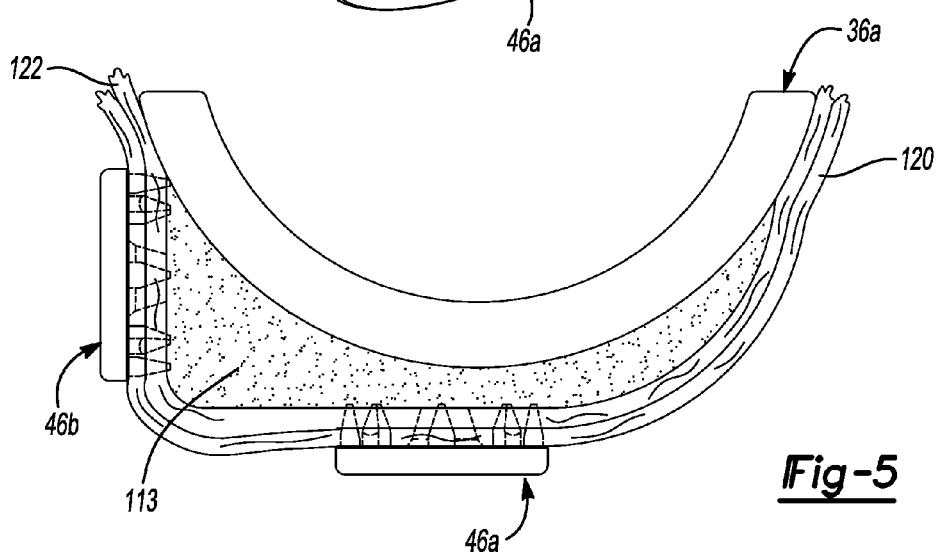

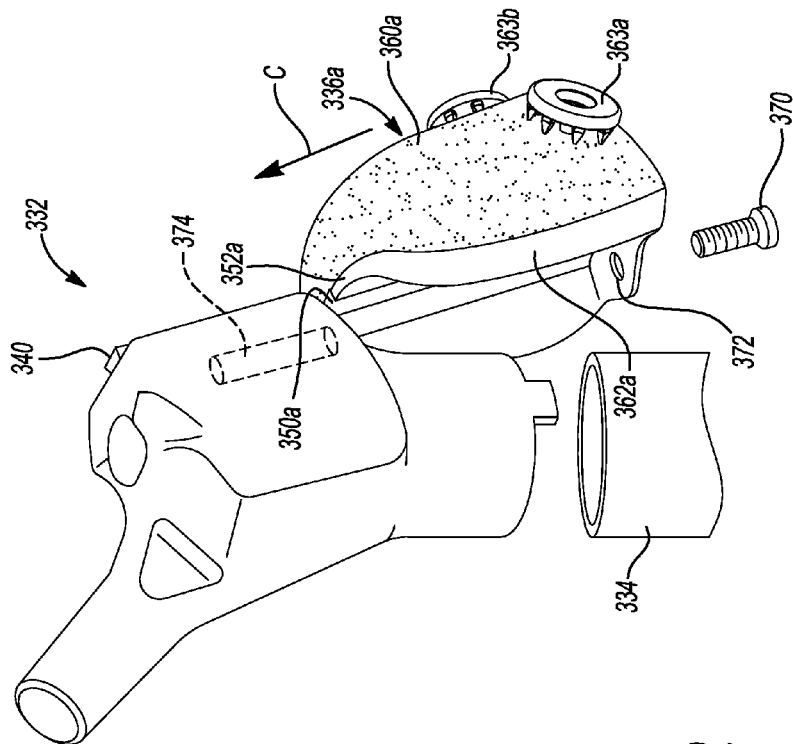
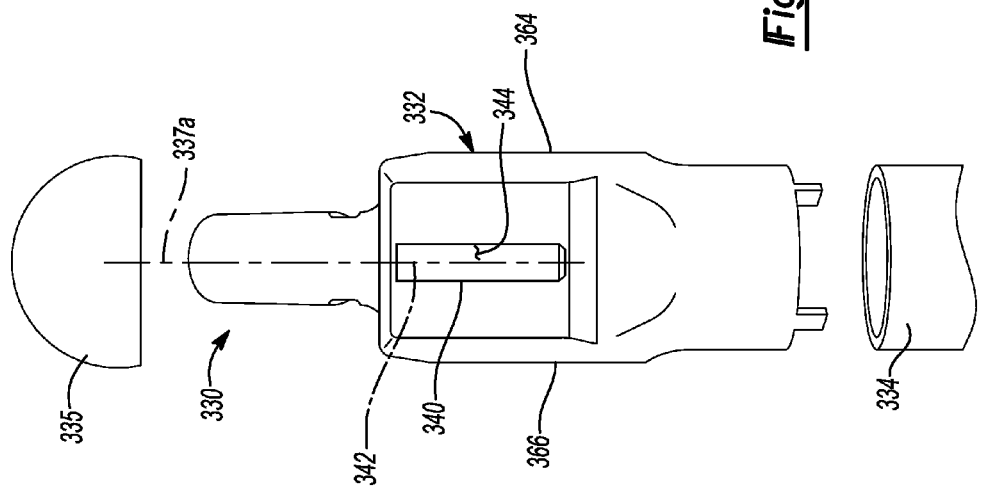

MODULAR ATTACHMENT MECHANISM IN PROSTHETIC IMPLANTS

FIELD

The subject disclosure is related to prosthetic implants positioned in an anatomy, and particularly to modular mechanisms for soft tissue attachments to prosthetic implants.

BACKGROUND

A prosthesis can be positioned in a subject, such as a human patient, for replacing a portion of an anatomy. Portions of anatomy may be required to be replaced due to disease, injury, or other reasons. For example, a prosthetic implant can be positioned in a femur to replace a portion of the proximal femur, including at least a femoral head, due to disease or wear of a natural femoral head. When preparing an anatomy for the prosthesis, however, soft tissue portions and boney portions of the anatomy may need to be removed. For example, the femoral head is near a greater trochanter to which several soft tissue, including muscle attachments, occur. An extensor muscle is connected to the greater trochanter. During preparation of the femur for the prosthesis, the proximal femur including the greater trochanter may need to be resected. In this case, resection or removal of the extensor muscles may be necessary.

SUMMARY

A proximal femoral prosthesis can be positioned to replace a portion of a femoral head and can also include portions allowing for connection of soft tissue that is disconnected during resection of a proximal femur. For example, as discussed above, during resection of the proximal femur, a greater trochanter may be completely or partially resected thereby disconnecting the extensor muscle from the femur. The proximal femoral prosthesis can include an area for allowing reconnection of the soft tissue to the proximal femur prosthesis.

The proximal femoral prosthesis, however, may not always need to replace a portion of the greater trochanter and/or the extensor mechanism may be resected entirely. Accordingly, a soft tissue connection portion can be modular to be connected to the femoral prosthesis only when a greater trochanter is necessary to be resected in a procedure. Additionally, the modular soft tissue connection portion can include various shapes and sizes to be selected for optimal connection area of the soft tissue to the prosthesis. In other words, described herein is a method and apparatus to provide for connection areas of soft tissue in one or more anatomical mimicking locations, including lateral, medial, posterior, and anterior. According to various embodiments, a modular soft tissue attachment portion can be connected to the proximal femoral prosthesis to allow for connection of soft tissue to the proximal femoral prosthesis. For example, the modular soft tissue connection or attachment portion can allow connection of an extensor muscle to the proximal femoral prosthesis member and can include a plurality of positions and in a large or different areas for connection of the soft tissue.

According to various embodiments, a soft tissue portion can be selected to be connected to a soft tissue connection portion of a prosthesis in at least two positions. This can include selecting at least a first soft tissue connection region and a second soft tissue connection region spaced apart from the first soft tissue connection region. Wherein the selection and/or connection includes selecting an anatomical re-creation of a soft tissue connection to a resected greater trochanter of a patient. The soft tissue selected for connection can include a hip extensor mechanism.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4 is a top view of a femoral prosthesis with a soft tissue connection portion, according to various embodiments;

FIG. 5 is a top view of the femoral prosthesis of FIG. 4 with soft tissue connected to the soft tissue connection portion;

FIG. 9 is a lateral elevational view of a femoral prosthesis, according to various embodiments;

FIG. 10 is a prospective view of a femoral prosthesis with an exploded soft tissue connection portion, according to various embodiments;

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. Furthermore, different features of separately discussed examples can be combined as understood by one skilled in the art.

It is understood, as used herein, that intraoperative can refer to an action taken by a user, such as a selection or connection, after beginning an operative procedure. The beginning of an operative procedure can be understood to be a time after a surgeon has scrubbed and otherwise prepared for a surgical procedure. It can also include after preparing a subject for an incision or making an incision in a subject, such as the patient.

Figure 1:
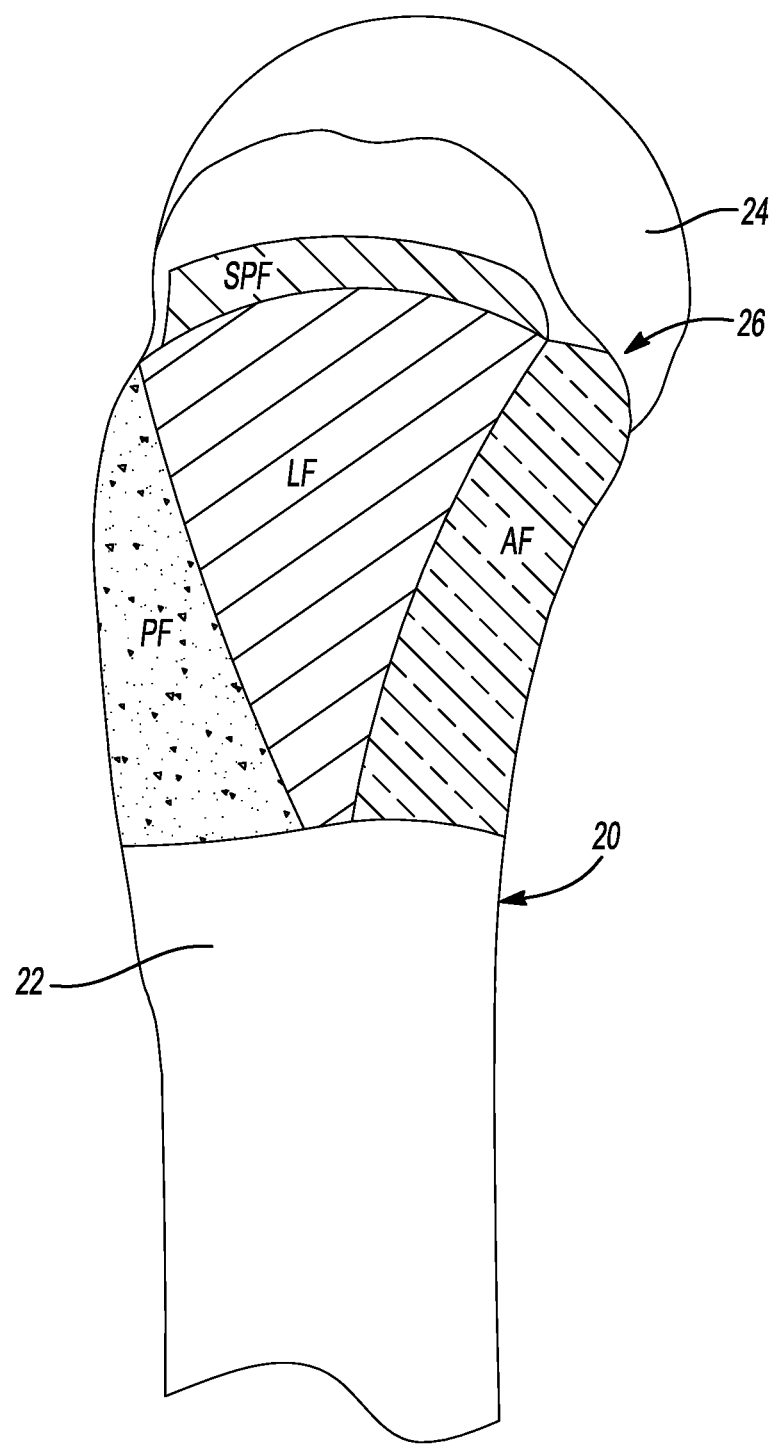
FIG. 1 is a lateral plan view of a greater trochanter in femur of a natural patient.

With reference to FIG. 1, a natural femur 20 of a human can include a shaft 22 and a femoral head 24. A greater trochanter 26 can include areas for connection of soft tissue, such as an extensor muscle. The greater trochanter can include attachments regions in substantially three dimensions around the greater trochanter 26. These connection regions can include, as schematically illustrated in FIG. 1, an anterior facet (AF) and lateral facet (LF), a posterior facet (PF), and a superior posterior facet (SPF). The four facets for attachment of soft tissue to the greater trochanter allow for soft tissue connection substantially around the greater trochanter 26 in all of the areas substantially not impeded by movement of the femur 20 relative to an acetabulum or a pelvis of a patient. Accordingly, a soft tissue attachment prosthesis can include a surface with regions that extend around the greater trochanter prosthetic area as well. That is, a soft tissue connection portion can include a plurality of separated soft tissue connection regions on the soft tissue connection region (e.g. the regions separate from the connection to the neck or stem portion) of the soft tissue connection portion.

Figure 2:
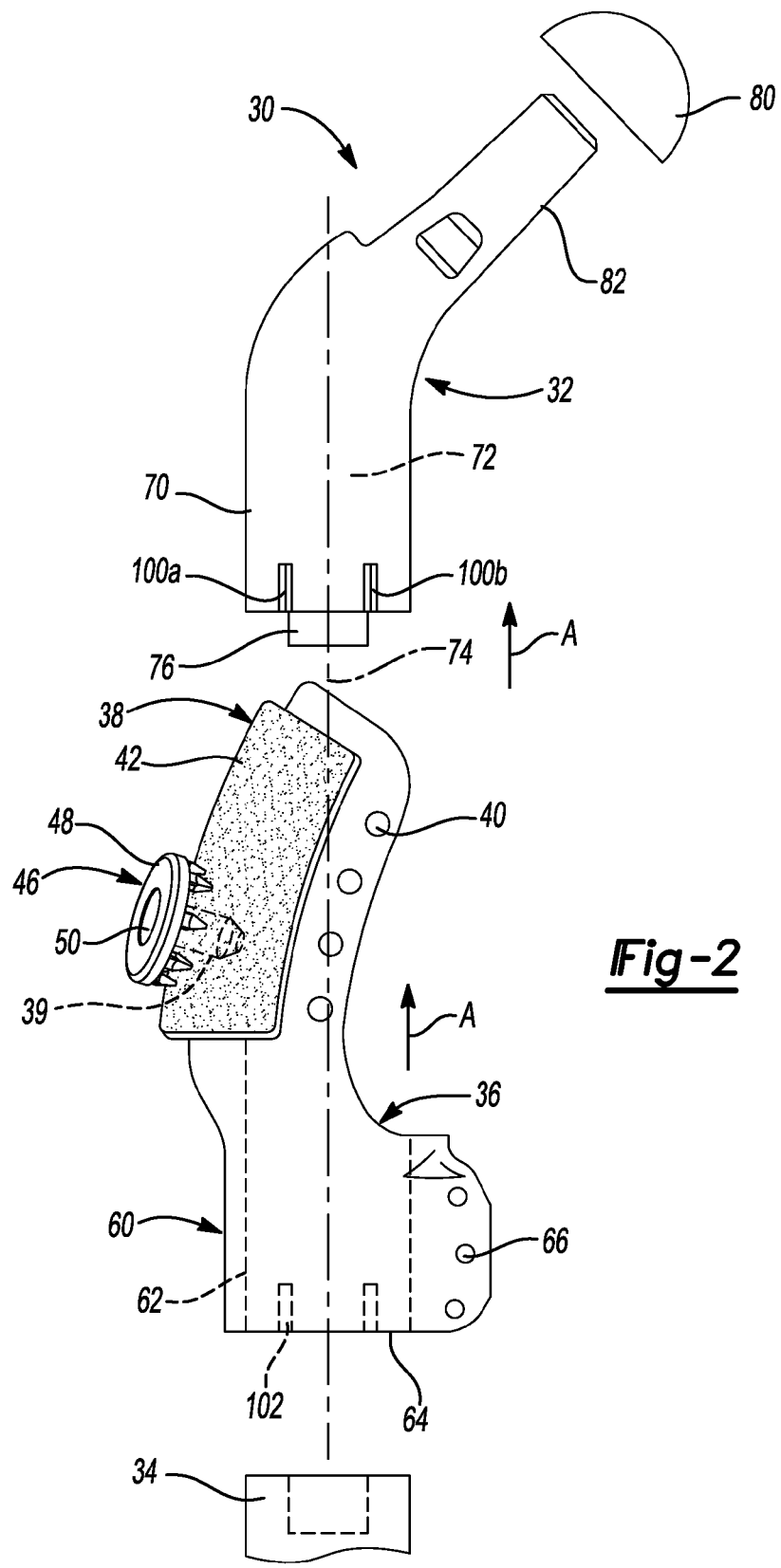
FIG. 2 is an exploded view of a femoral prosthesis having a soft tissue connection portion, according to various embodiments.

With reference to FIG. 2, a proximal femoral prosthesis 30 (also referred to solely as a proximal prosthesis) is illustrated. The femoral prosthesis 30 can include a neck portion 32 and a stem portion 34. Optionally interconnected to the neck portion 32 can be a greater trochanter prosthesis or soft tissue attachment prosthesis portion 36. The soft tissue prosthesis 36 is optional and may not be necessary for a selected surgical procedure. For example, if a femoral head, such as the femoral head 24 of the femur 20, is resected and the soft tissue connection regions of the greater trochanter 26 can be saved, then the soft tissue prosthesis 36 may not be necessary. In the case where the soft tissue connection regions of the greater trochanter 26 can be saved the femoral prosthesis 30 including generally only the neck portion 32 and the stem portion 34 can be positioned within the femur 20 to replace the resected femoral head 24. Thus, the soft tissue attachment 36 as a part of a prosthetic system is modular and optional. The soft tissue attachment 36 can be provided for intraoperative selection and connection to the femoral prosthesis 30 by a user, such as a surgeon.

If the greater trochanter 26 is resected then the soft tissue attachment 36 can be interconnected to the modular neck portion 32. The soft tissue attachment portion 36 can include one or more soft tissue attachment regions 38 that can include, optionally, bores or holes 40 for soft tissue attachment, such as for passing a wire or suture to anchor tissue, and a porous region 42. The porous region 42 is optional and can include porous materials, such as plasma coatings and porous metal constructs such as Regenerex® porous metal sold by Biomet, Inc. or additively manufactured constructs. The soft tissue attachment region 38 can also include bores 39, such as tapped bores, for connection of soft tissue connection or immobilization systems 46 that can include a washer or spiked washer 48 and a screw 50 that passes through the spiked washer 48 into the bore formed in the soft tissue attachment portion 38. Such spiked washers can include those disclosed in U.S. Pat. No. 8,118,868, incorporated herein by reference in its entirety. The connection system 46 can provide an initial fixation of soft tissue to the soft tissue connection portion while the porous region 40 can provide a frictional holding of the soft tissue and a region for soft tissue ingrowth. Similar soft tissue connection portions and porous regions can be provided for similar purposes in various embodiments, including those discussed herein.

Figure 3:
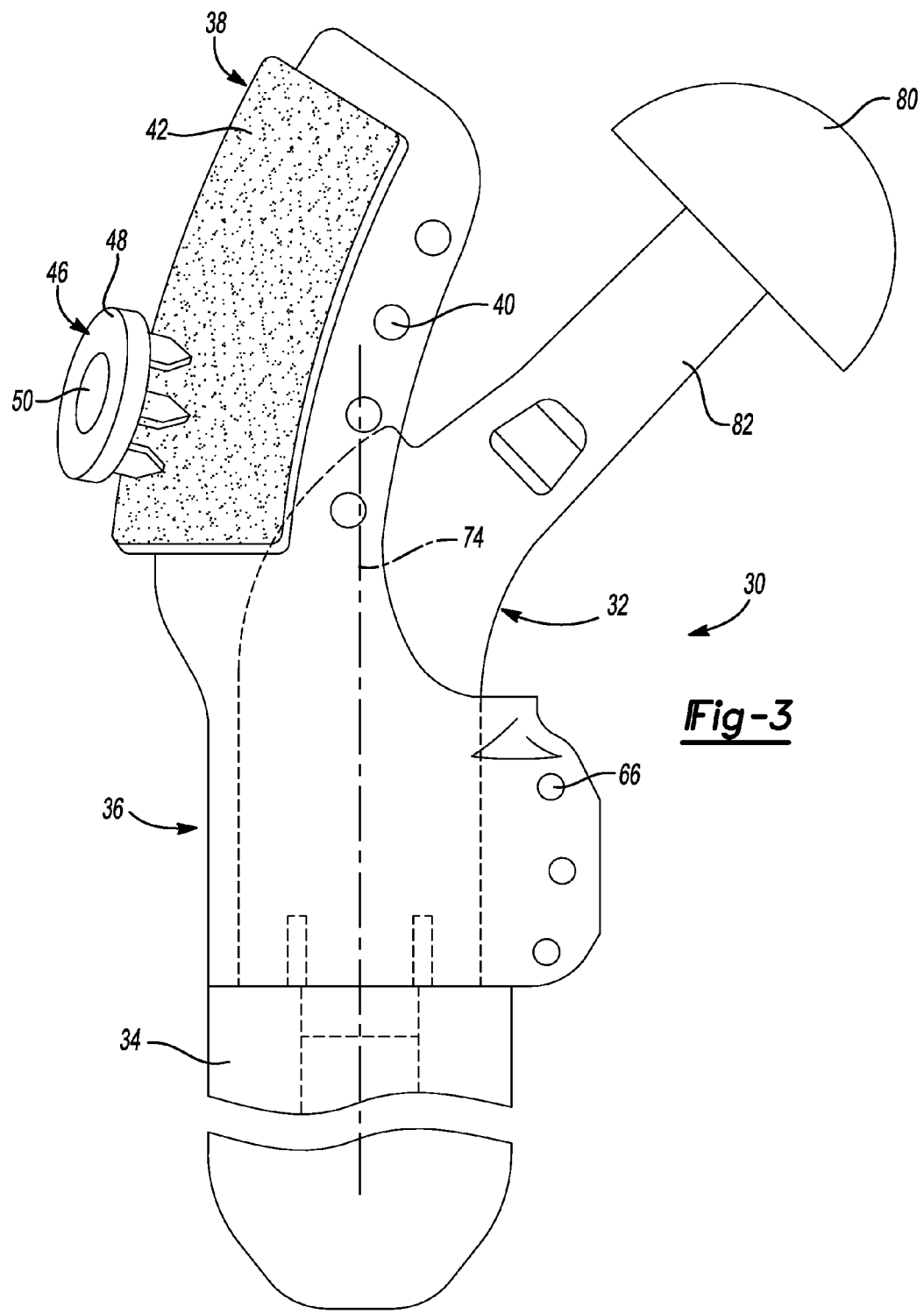
FIG. 3 is an assembled prospective view of the prosthesis of FIG. 2.

The soft tissue connection region 38 can be provided in a shape to assist in providing anatomical matching connection regions for soft tissue connection. For example, the soft tissue connection portion 38 can extend superiorly of the stem 34 and near and/or adjacent to the prosthetic head 80, as illustrated in FIG. 3. Moreover, the soft tissue connection portion can include an arc that curves around the neck 82, as illustrated in FIG. 3. Thus, the soft tissue connection region 38 can substantially mimic each and/or all of the facets of the natural femur 20, as illustrated in FIG. 1. Further, the soft tissue connection region 38 can provide the soft tissue connections 40 at an inferior position while the porous region extends superiorly therefrom.

Extending from the soft tissue connection region 38 of the soft tissue prosthesis member 36 can be a neck attachment region 60. The neck attachment region 60 can include a bore or passage 62 formed through a connection member 64. The passage 64 can be tapered to assist in connection to a taper region 70 of the neck portion 32. The connection member 64 can also define passages 66 for sutures, wire, suture anchors or other selected attachment portions. The prosthetic neck portion 32 can include the taper region 70 that can be positioned through the passage 62. Generally, the soft tissue prosthetic member 36 can be moved in the direction of arrow A to slide over the taper region 70 of the prosthetic neck portion 32 to engage the prosthetic neck member 32. It is understood that the taper region 70 can form a taper lock with the passage 62 or can simply provide an interference of the prosthetic neck portion 32 relative to the prosthetic soft tissue attachment 36. The taper neck region 70 can define a taper angle 72 relative to a central axis 74 of the prosthetic neck portion 32. The taper angle 72 can be selected for connection of the soft tissue connection portion 36 relative to the prosthetic neck portion 32. Additionally, the taper angle 72 can be selected for allowing for ease of removal and disconnection of the soft tissue prosthetic portion 36 relative to the neck portion 32.

Once the soft tissue prosthesis portion 36 is connected to the prosthetic neck portion 32, the stem 34 can be connected with the prosthetic neck portion 32 and in the appropriate manner, such as an interconnection of the stem 34 with a mating portion 76 of the prosthetic neck portion 32. It is understood that other locking features can also be provided, such as a locking screw that passes through the prosthetic neck portion 32 to engage the stem 34 as is generally included in the OSS™ Orthopedic Salvage System prosthesis, sold by Biomet, Inc.

Additionally, a prosthetic head 80, according to an appropriate design or configuration can connect with a neck 82 of the prosthetic neck portion 32. The neck 82 can include a male taper, such as a self-locking taper, that engages a female taper formed in the head 80 to allow for connection of the head 80 relative to the neck portion 32. It will be understood that the male and female tapers can be revered between the neck portion 32 and the head 80. Appropriate connections of heads and types of heads are included in the prosthetic or prosthesis system OSS™ Orthopedic Salvage System, sold by Biomet, Inc.

As illustrated in FIG. 3, the assembled prosthesis 30 can include the soft tissue connection member 36 interconnected with the neck portion 32 and the stem portion 34. The assembly 30 can be implanted to replace the resected femoral head and greater trochanter of the femur 20. The femur 20 includes the greater trochanter 26 that is naturally positioned relative to the femoral head 24 and the shaft 22 of the femur in a selected natural anatomical configuration. The anatomical configuration, however, can also vary from patient to patient. Accordingly, the passage 62 can include a keyed portion, such as a portion that is non-cylindrical or including a projection or depression to receive or engage a projection or depression of the neck portion to allow for selectively and fixedly rotationally positioning the soft tissue connection 38 relative to the neck 82 of the neck portion 32, including around the axis 74. It is also understood that a keyed configuration is not necessary and that only a smooth taper or surface can be provided. In this manner, the neck portion 32 and the soft tissue connection 38 can be connected in any selected rotational orientation.

Returning reference to FIG. 2, the taper region 72 can include a depression or groove 100 that can engage a projection 102 at the soft tissue connect portion 36. The neck portion 32 can include a plurality of the grooves, 100a, 100b to allow for rotationally positioning the modular soft tissue prosthetic member 36 relative to the neck 82 of the neck portion 32. The grooves 100 can be provided in any selected number around the taper region 72 or any appropriate region of the neck member 32. Accordingly, the soft tissue prosthesis member 36 can be rotationally positioned at different and selected positions relative to the neck 82 of the neck portion 32.

As illustrated in FIG. 4, the soft tissue prosthetic member 36 can include a plurality of sides as illustrated as soft tissue connection portion 36a. It is understood that the plurality of sides as a plurality of connection regions can be included in the prosthetic portion 36 illustrated in FIGS. 2 and 3 or the soft tissue connection region 38 can include a radius or single curved portion. The single curved portions can also define a plurality of spaced-apart connection regions that can be used to mimic the natural connection regions illustrated in FIG. 1, as discussed above.

The soft tissue connection portion 38 of the tissue connection portion 36 can include, either alternatively to the radius or in addition to the radius, a first or major side 110 and a second or minor side 112. For example, the sides 110, 112 can be formed of porous material at the porous tissue connection region 40. The sides 110, 112 can be positioned relative to the neck 82 via the interconnection of the projection of 102 with one or more of the grooves 100. Accordingly, as illustrated in FIG. 4, the major side 110 is substantially lateral of the neck 82. It is understood, however, that the major surface 110 can be rotated around the axis 74 of the neck portion generally in the direction of double-headed arrow B. In this way the major and minor surfaces 110, 112, can be positioned relative to the neck 82 at a selected natural anatomical configuration to mimic or provide for substantially anatomical matching connection regions for the soft tissue. The natural anatomical configuration, including the relative locations of the facets to the natural femoral head 24, can be determined after incision into a patient to the view the femur 20 or with imaging prior to the beginning of a procedure. The natural anatomical configuration can then be mimicked, at least as close as possible, by selectively positioning the soft tissue connection portion relative to the neck portion 32.

The major surface 110 can meet the minor surface 112 at a raised peak or hump 113. The peak 113 can include a thickened porous region. In addition, the peak can provide additional frictional holding of soft tissue placed near the peak 113, as illustrated below.

For tissue connection and fixation, soft tissue can be wrapped around the soft tissue connection region 38 such that it engages both the major surface 110 and the minor surface 112. Additionally, the porous portion 42 of the soft tissue connection region 38 can provide an initial friction holding connection of the soft tissue with the soft tissue connection region 38 and for long-term ingrowth of the soft tissue to the soft tissue connection region 38. The connections 46, or other appropriate locking portions, can be provided to create initial and/or localized immobilization of the soft tissue. As discussed above, the supplemental or additional soft tissue connection portions, including the screw and washer lock systems 46, including one or more washer lock systems 46a and 46b, can be used to additionally interconnect the soft tissue with the soft tissue connection portion 36. Thus, both non-compressed tissue is provided for tissue ingrowth in addition to immobilization, at a spaced apart location, of the soft tissue connection portion 32. These connection regions can provide substantially anatomical matching connections of the soft tissue to mimic and/or copy the natural anatomical facets as illustrated in FIG. 1.

With reference to FIG. 5, the soft tissue can include a first piece 120 and a second soft tissue piece 122 that both interconnect with the soft tissue connection region 38. Additionally, both pieces of the soft tissue 120, 122 can wrap around to contact both of the major and minor surfaces 110, 112 of the soft tissue connection region 38. Accordingly, upon implantation and connection of the soft tissue pieces 120, 122, a substantial re-creation of the soft tissue connection from the natural anatomy, as schematically illustrated in FIG. 1, can be replicated due to the multiple surfaces and the selectable position of the soft tissue connection member 36.

Additionally, the major and minor surfaces 110, 112, as discussed above, can include additional facets that can be formed on these surfaces. The facets allow for creation of places or regions of attachment, including the four regions illustrated in FIG. 1, such as the posterior facet, the lateral facet, the anterior facet, and the superior posterior facet. Accordingly, the interconnection or keyed relationship of the soft tissue connection portion 36 relative to the neck portion 32, such as with the projections and grooves 100, 102, can allow for selective orientation of the various facets relative to a natural anatomy. Accordingly, soft tissue can be interconnected with the prosthesis in an appropriate and selected anatomical configuration. By allowing the soft tissue to be connected in a substantially natural anatomical configuration, biomechanics of a patient can be more substantially recreated after the prosthesis is implanted.

Figure 6:
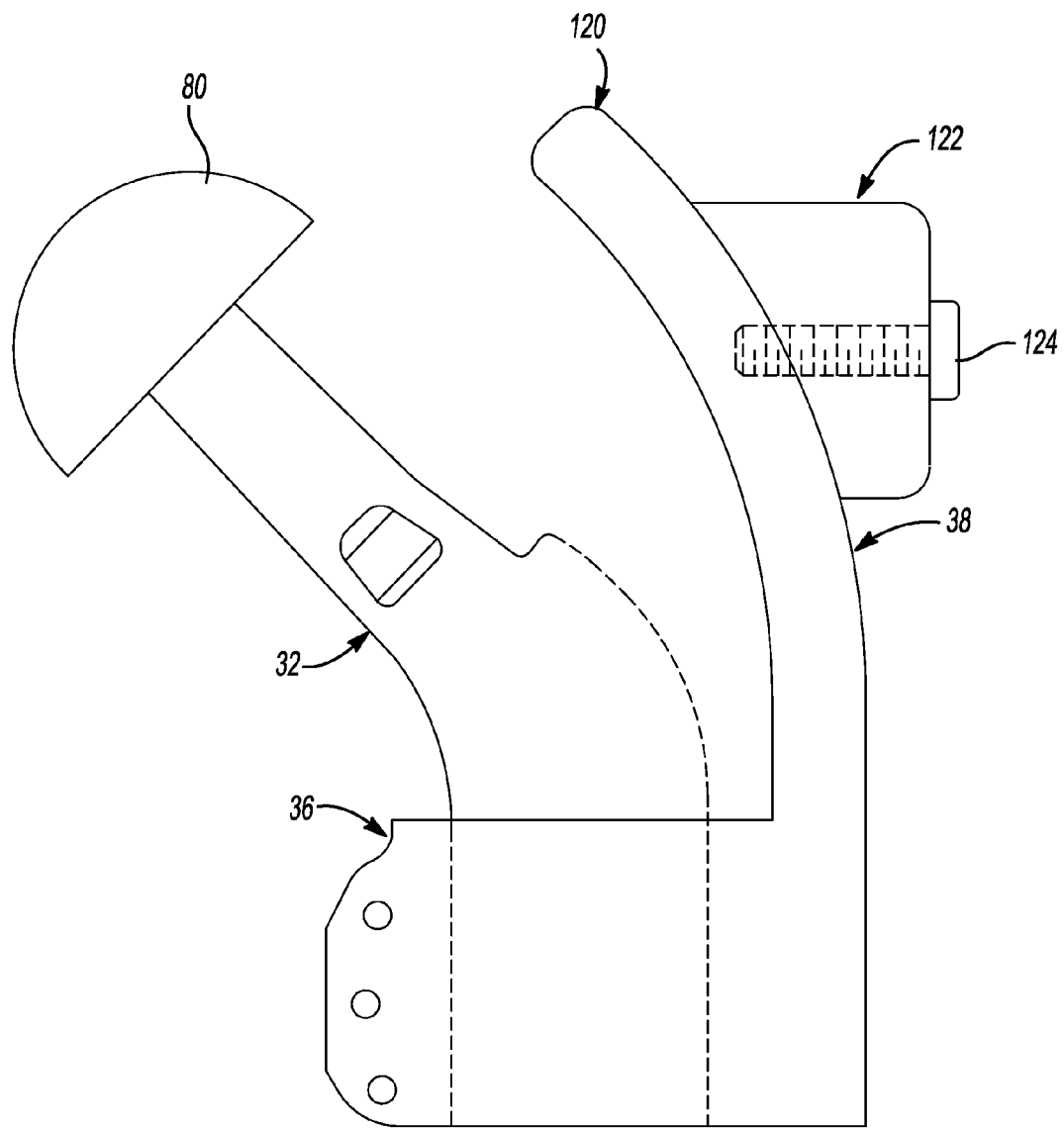
FIG. 6 is an elevational view of a femoral prosthesis and soft tissue connection portion, according to various embodiments.

With reference to FIG. 6, the soft tissue connection portion 36 can include a soft tissue attachment region, according to various embodiments, that includes a substantially superior extending region 120. The extending region 120 can also extend medially over or towards the neck 82. The superior extending region 120 can be a portion of the soft tissue attachment region 38 and can be formed of selected materials, such as porous coated materials or completely porous metal constructs formed from metal materials such as Regenerex® porous metals, sold by Biomet, Inc. and/or additive manufacturing techniques. The superior region 120 can extend over a superior portion of the neck portion 32, such as that substantially co-extensive with the neck 82 of the prosthesis 30. The superior portion soft tissue connection region 120 can allow for connection of soft tissue in a region superior of the femur 20. The length of the superior portion 120 can be provided especially in an instance where soft tissue extending from a superior region is resected. The length of the superior extending portion 120 does not require soft tissue to extend as far towards the stem 34 as when the superior region 120 were not provided.

The soft tissue connection portion 36 can further be augmented or provided with one or a plurality of soft tissue connection augments 122. The soft tissue connection augments 122 can be formed of selected materials, including porous coated metals and/or porous constructs such as Regenerex® porous metal sold by Biomet, Inc. or additively manufactured constructs. The soft tissue augment portions 122 can be connected with the soft tissue connection region 36 to provide a selected shape or to provide for additional or selectively positioned soft tissue connection surfaces. As illustrated in FIG. 6, the supplemental or augmented soft tissue connection portion 122 can be fixed to the soft tissue connection region 38 with a fixation member, such as a screw 124. As specifically illustrated in FIG. 6, the augmented soft tissue connection portion 122 can be positioned near the superior connection portion 120 to assist in further enhancing or enlarging an area for fixation of soft tissue relative to the soft tissue portion 36. Accordingly, and according to the various embodiments disclosed herein, the soft tissue connection portions can be augmented with additional modular portions 122 to provide for selected soft tissue connection regions. It is understood that the augmented soft tissue connection portion 122 can be provided in the appropriate shape or configuration for soft tissue connection. Additionally, the augmented soft tissue portions 122 can be provided in a kit, such as the kit 600 discussed below for selection by a user intraoperatively during a procedure. The kit 600 can also include a plurality of the modular portions 122 including differing sizes, shapes, etc.

Additionally, it will be understood, that the prosthesis can be implanted substantially only with the neck portion 32 and the stem portion 34 to allow for a configuration when the greater trochanter need not be resected or substantially resected. Thus, the prosthesis assembly 30 can allow for selection of replacement of the soft tissue connection member 36 or without the soft tissue connection member 36.

Figure 7:
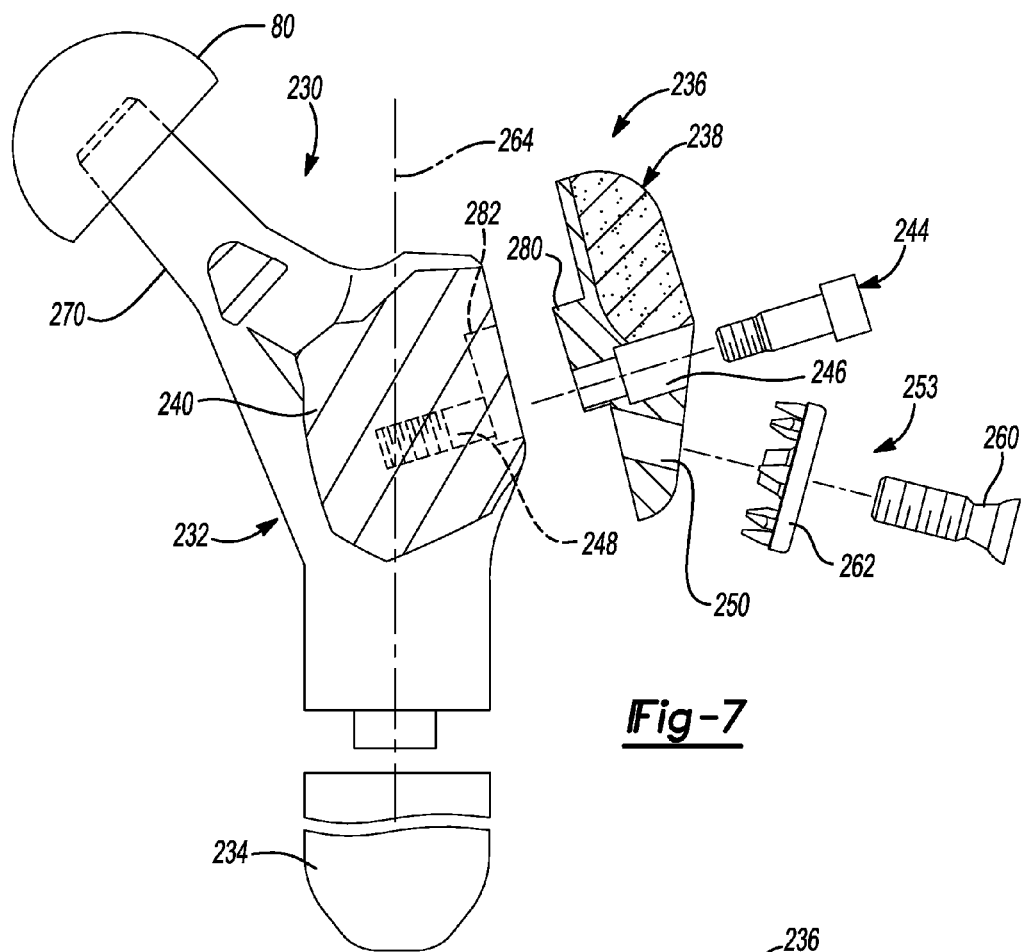
FIG. 7 is a side elevational exploded view of a femoral prosthesis and soft tissue connection portion.
Figure 8:
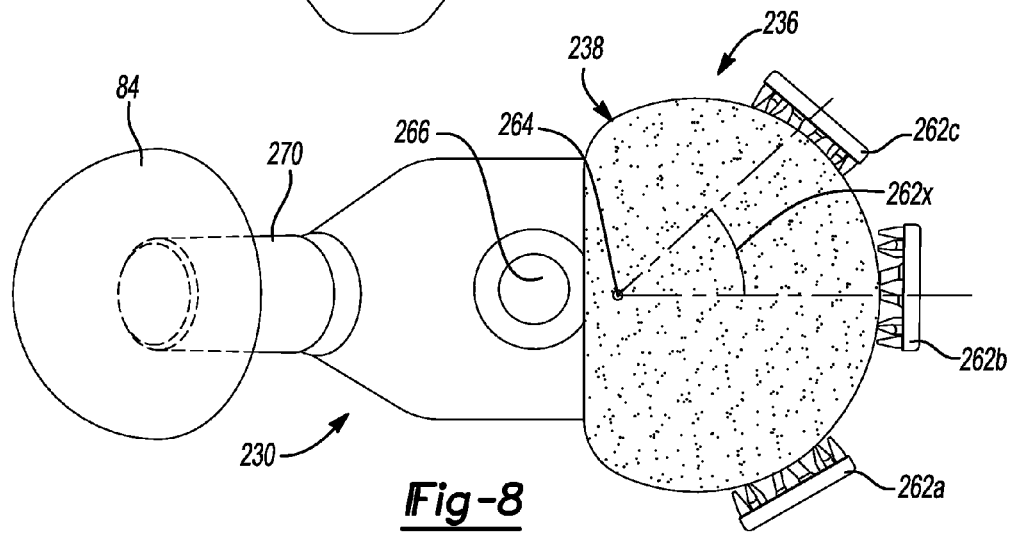
FIG. 8 is a top elevational view of an assembled prosthesis according to FIG. 7.

According to various embodiments, as illustrated in FIGS. 7 and 8, a prosthesis 230 can include a neck portion 232 that can be interconnected with a stem 234 and a soft tissue connection portion 236. The various portions of the prosthesis 230 can be similar, at least in function and placement of the respective portions, including the stem portion 34, the neck portion 32, and the soft tissue connection portion 36, as discussed above. As illustrated in FIGS. 7-8, and discussed below, the prosthesis 230 can be provided in a different configuration as discussed in detail herein. Also, the soft tissue connection portion 236 is optional.

As initially illustrated in FIG. 7, the neck prosthesis 232 can be implanted into the femur 20 with the stem 234 in a configuration that does not include a connection of the soft tissue connection portion 236. Accordingly, as discussed above, the neck prosthesis 232 can be positioned in the femur 20 without requiring a portion for reattaching soft tissue. This allows for an intraoperative selection of a prosthesis with or without a soft tissue connection portion. In a configuration where a soft tissue connection is not selected, a flat or smooth side 240 is provided to allow for positioning of the prosthesis relative to the femur 20.

Nevertheless, the soft tissue portion 236 can be interconnected with the neck portion 232 to allow for soft tissue connection to a soft tissue connection region 238. The soft tissue connection region 238 can include porous material, including porous coated metals and/or porous constructs such as Regenerex® porous metal sold by Biomet, Inc. or additively manufactured constructs. A bolt 244 can be passed through a passage 246 to connect the soft tissue connection portion 236 to the femoral neck portion 232. The femoral neck portion 232 can define a passage 248 to engage or connect with the bolt 244, such as with a threaded interconnection between the bolt 244 and the passage 248 in the neck portion 232.

Additionally, the soft tissue connection portion 236 can define a second bolt passage 250. The second bolt passage 250 can allow for connection of a soft tissue connection system 253 where a bolt or screw 260 can pass through a spiked washer 262 to engage the passage 250 in the soft tissue connection portion 236. As discussed above, the soft tissue connection system 253 with the soft tissue connection portion 236 can provide for at least an initial connection or immobilization of soft tissue relative to the soft tissue connection portion 236. As illustrated in FIG. 7, the soft tissue connection system 253 can be positioned substantially inferior on the soft tissue connection portion 236 such that a major portion or large portion of the soft tissue connection region 236 is substantially mobile until tissue ingrowth occurs. Friction between the soft tissue and the connection region 238, however, can assist in holding the soft tissue in a selected location. Moreover, the inferior placement of the soft tissue connection system 253 allows for a large and uninterrupted portion of the connection region 238 to be provided for soft tissue ingrowth.

With additional reference to FIG. 8, the soft tissue connection portion 236 can include a configuration that has an arc or radius and/or can include sides, such as the major and minor sides 110, 112 discussed above. As illustrated in FIG. 8, however, a radius of the soft tissue connection portion can substantially wrap around or define an arc, such as at least about an 180° arc relative to a central axis 264 of the prosthetic neck portion 232. The central axis 264 can be formed or defined through a locking bolt hole 266 through which a locking bolt can pass to engage the stem 234 to lock the neck portion 232 to the stem 234. The axis 264 can also be defined relative to the soft tissue connection portion 236 alone. The soft tissue connection portion 236, therefore, could be used to engage soft tissue in substantially anatomical connection regions to mimic the natural anatomical configuration, as discussed above.

Additionally, as discussed above, a plurality of the locking washers 262a, 262b and 262c can be provided at various positions on the soft tissue connection portion 236 to assist in creating the substantially anatomical connection positions or regions. Although it is not required to include at least three of the washers 262a-262c, a selected number can be provided, such as intraoperatively selecting a number, to provide for an appropriate or selected connection of the soft tissue relative to the soft tissue connection portion 236. The washers 262a-262c can be radially displaced at a selected angle 262x apart around the arc of soft tissue connection portion 236. The prosthesis 230 can also be positioned in the femur 20 to include a head 84 interconnected with a stem 270.

The soft tissue connection portion 236 can include a projection 280 that can include a keyed configuration, such as a non-circular configuration, or a circular configuration with projection 280 to be received in a depression 282 of the neck portion 232. If the projection 280 is a keyed projection, the soft tissue connection portion 236 can be rotated relative to the neck portion 232 to allow for a selected position or orientation of the soft tissue connection portion 236 relative to the neck portion 232 in one of a plurality of possible locations and/or configurations. It is understood, however, that the soft tissue connection portion 236 can be connected to the neck portion 232 in any selected, such as a single selected, configuration or location. The soft tissue can then be connected to the soft tissue connection portion 236 once the prosthesis 230 is positioned within the anatomy.

Figure 11:
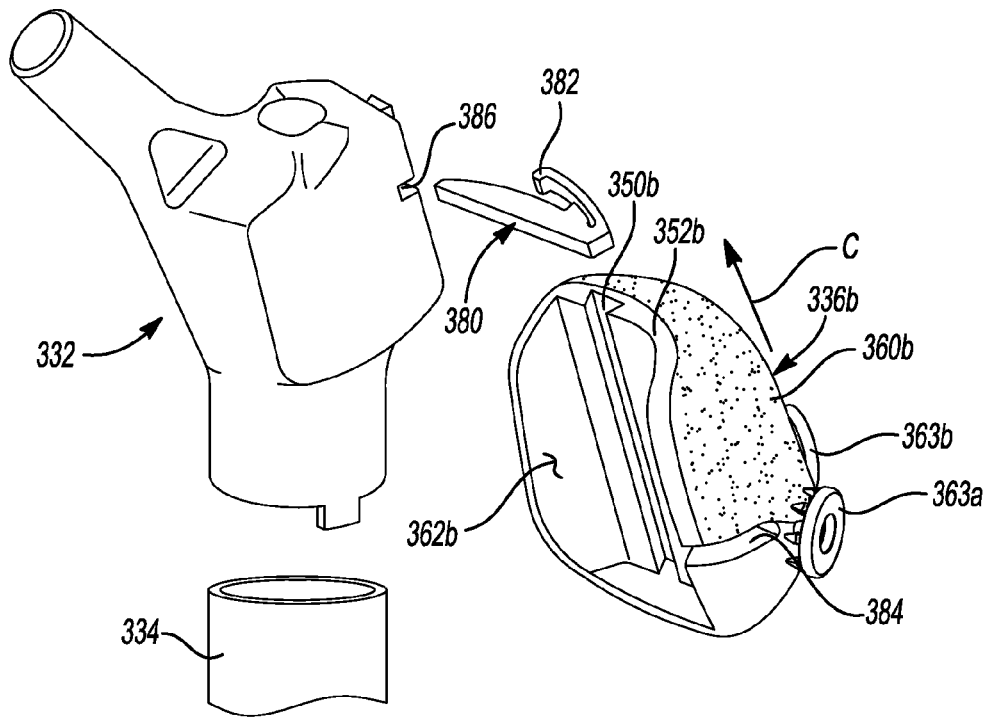
FIG. 11 is an exploded prospective view of a femoral prosthesis of the soft tissue connection portion, according to various embodiments.

With reference to FIGS. 9-11, a femoral prosthesis 330, according to various embodiments can include a neck portion 332 to which a stem 334 can be connected. A head 335 can also be connected to a neck 337, as discussed above. The neck 337 can also define an axis 337a. A soft tissue connection portion 336a, as illustrated in FIG. 10, or 336b, as illustrated in FIG. 11, can be interconnected with a dovetail rail 340. The dovetail rail 340 can define a central axis 342 and an outer edge can form an angle 344 relative to the central axis 342. The angle 344 can be an appropriate angle such as about 20° to about 40°, including about 2° to about 3°, and further including about 2°. The dovetail rail 340 can allow for a sliding interconnection or a sliding positioning of the soft tissue connection portion 336a and 336b by sliding a respective dovetail groove 350a and 350b formed through a surface, such as a superior surface 352a and 352b of the respective soft tissue connection portions 336a and 336b. Generally, the soft tissue connection portions can be slid onto the dove-tail rail 340 generally in the direction of arrow C. It is understood, however, that the dovetail rail can be formed on the respective soft tissue connection portions 336a and 336b and the dovetail groove can be formed into the neck portion 332. This reverse configuration would still allow the respective soft tissue connection portions 336a and 336b to be slid onto the neck portion 332.

As is illustrated in FIGS. 10 and 11, the arrow C is in the direction of a superior portion of the prosthesis 330, which generally a superior position in an implanted position of the patient. Accordingly, when soft tissues are connected to the soft tissue connection portions 336a and 336b, the forces applied by the soft tissue on the soft tissue portions 336a and 336b are generally in the same direction as arrow C. As the dovetail rail 340 tapers outwardly at the angle 344, the movement of the soft tissue connection portions 336a and 336b in the direction of arrow C further will lock and engage the soft tissue connection portions 336a and 336b with the neck portion 332 due to interaction with the dovetail rail 340 and the respective grooves 350a and 350b. In addition, a stop projection or portion can be formed opposite the opening for the groove 350a, 350b to engage the dovetail rail 340 to stop movement of the soft tissue connection portion 336a, 336b.

The soft tissue connection portions 336a and 336b can include exterior soft tissue connection regions 360a and 360b. The soft tissue connection regions 360a, 360b can include the porous coat or porous constructs discussed above, including Regenerex® porous metal sold by Biomet, Inc. or additively manufactured constructs. The soft tissue connection regions can be formed over an interior or substrate that defines the respective grooves 350a and 350b and also an internal surface or area 362a, 362b that can fit over and/or around sides 364 and 366 of the neck portion 332. Accordingly, the soft tissue connection portion 336a, 336b can surround a portion of the neck component 332 similar to the soft tissue connection portion 336 discussed above.

Accordingly, the soft tissue connection portions 336a, 336b can allow for a connection of soft tissue at a plurality of positions of a plurality of regions relative to the neck portion 332. The plurality of regions or areas of connection can allow for a recreation of the natural soft tissue connection as illustrated in the natural femur in FIG. 1. For example, the exterior soft tissue connection regions 360a and 360b can define an arc having a radius, as discussed above. Further, the exterior soft tissue connection regions 360a and 360b can have straight surfaces, such as the major and minor sides, 110, 112. The exterior soft tissue connection regions 360a and 360b can be provided to define the anatomical matching connections to allow the implant to substantially mimic the anatomical facet connections.

Additionally, one or a plurality of soft tissue immobilization systems 363a, 363b can be provided to interconnect with the respective soft tissue connection portions 336a, 336b. The soft tissue connection or immobilization portions 363a, 363b specifically illustrated in FIGS. 10 and 11 can include a spiked washer or compression washer. Although not specifically illustrated in FIGS. 10 and 11 the washer can include a bore or passage for a screw to pass there through. The soft tissue connection portion 336a and 336b can define bores to receive and connect with the screws of the soft tissue immobilization portions 363a, 363b.

As illustrated in FIGS. 10 and 11, and discussed in relation to the soft tissue connection portion 236 illustrated in FIG. 8, the soft tissue connection regions 360a, 360b can extend a selected portion around a central axis the neck portion 332 such as about 180° or any selected amount. The porous areas soft tissue connection regions 360a, 360b can be used to frictionally hold the soft tissue in addition to or separately from the soft tissue immobilization portions 363a, 363b. As illustrated, the soft tissue immobilization portions 363a, 363b can be positioned substantially inferior relative to the implant 332 and/or the soft tissue connection regions 360a, 360b when the implant is positioned in the selected anatomy. This, according the various embodiments described herein, allows for a large, including greatest amount, of uninterrupted contact surface area between the soft tissue and the soft tissue connection regions 360a, 360b.

The soft tissue connection portions 336a, 336b can be slid onto the dovetail rails 340 as discussed above. As further discussed above, soft tissue connection on the soft tissue connection regions 336a, 336b can assist in locking and holding soft tissue connection portions 336a, 336b to the neck portion 332. In addition, locking, either permanently or for initial connection, members can be provided, for example as illustrated in FIG. 10, a locking or fixing screw 370 can be used to pass through a bore 372 in a bottom or selected wall of the soft tissue connection portions to engage a passage or bore 374 in the neck portion 332. The bore 374 can be formed near the dovetail rail 340 and can be threaded to engage threads on the locking screw 370.

Additionally, or in alternative to the locking screw 370, a locking bar 380 can be provided to interconnect the soft tissue connection portion 336b with the neck portion 332. The locking bar 380 can include a deflectable tab or arm 382. The locking bar can be pushed through a first passage 384 in a sidewall of the soft tissue connection portion 336b to engage a groove or slot 386 in the neck portion 332. The tab portion 382 can be deflected towards a main portion or inwardly to allow passage of the locking bar 380 through the wall passage 384. Once the tab arm 382 has moved through the passage 384 and passed at least a selected portion of a wall, the tab 382 can deflect outwardly or away from the arm portion to fixedly or lockingly engage the wall of the soft tissue connection portion 336b. In this way, the locking bar 380 can be held relative to the soft tissue connection portion 336b and the neck portion 332.

Accordingly, in various embodiments, the locking screw 370 or the locking bar 380 can be used to selectively fix the soft tissue connection portions 336a, 336b relative to the neck portion 332. It is understood that other selected locking configurations or members can be selected to lock the selected soft tissue connection portions 336a, 336b relative to the neck portion 332. Also, additional or alternative locking portions can be used.

Figure 12:
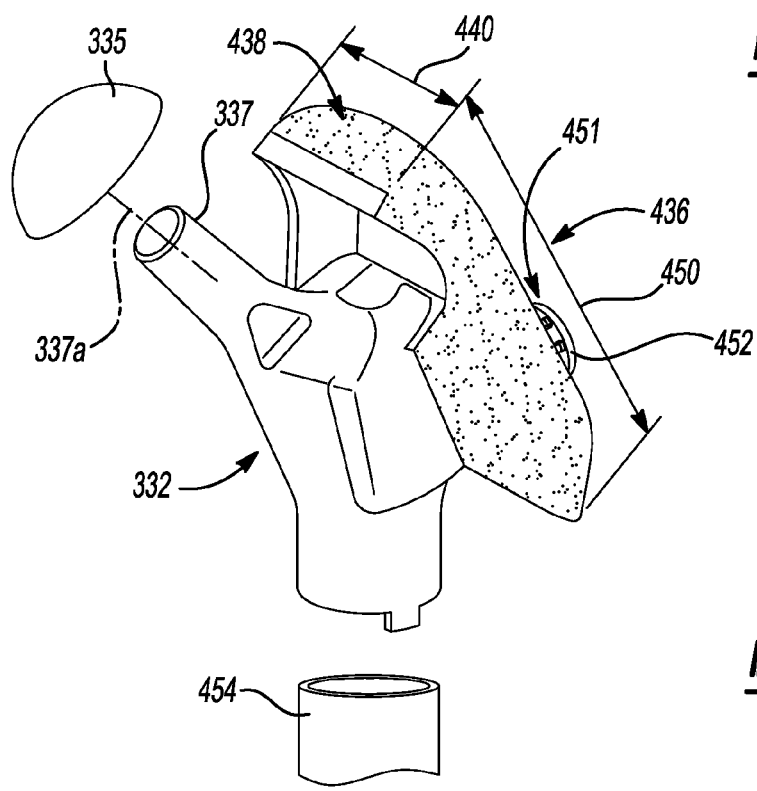
FIG. 12 is an assembled view of a femoral prosthesis with a soft tissue connection portion, according to various embodiments.
Figure 13:
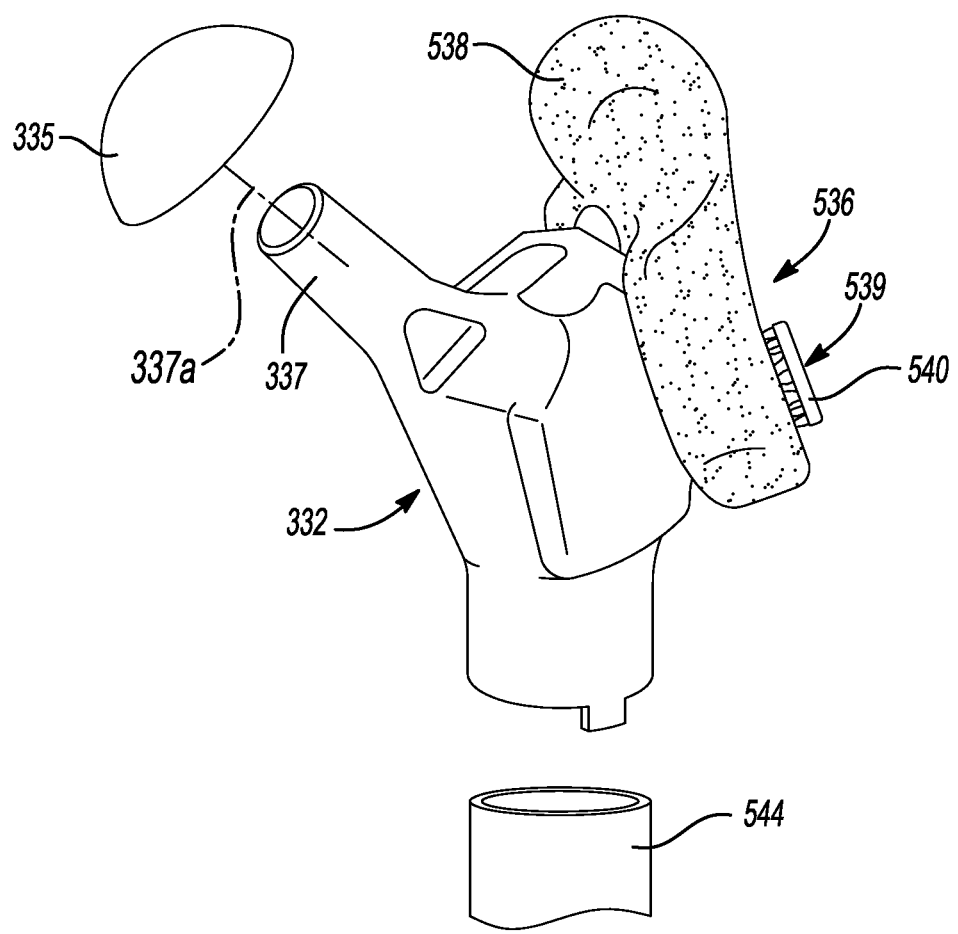
FIG. 13 is an assembled perspective view of a femoral prosthesis with a soft tissue connection portion, according to various embodiments.

As discussed above, the soft tissue connection portions, including the soft tissue connection portions 336a and 336b can include a selected configuration of the respective soft tissue connection regions to allow for positioning of the soft tissue relative to the neck portion 332. As illustrated in FIGS. 12 and 13, the soft tissue connection portions can include alternative or selectable shapes such as the soft tissue connection portion 436 illustrated in FIG. 12 or the soft tissue connection portion 536 illustrated in FIG. 13. The soft tissue connection portions 436, 536 can be interconnected with the neck portions in a selected manner, such as with a dove-tail connection, as illustrated in FIG. 12 or the screw or dovetail connection as illustrated in FIG. 13. Regardless, the soft tissue connection regions can include a superior connection portions and medial lateral collateral of selected designs.

As illustrated in FIG. 12, the soft tissue connection portion of 436 can include a superior soft tissue connection region 438 that is substantially wide or has a width 440 transverse relative to the central axis 337a of the neck 337 of the neck portion 332. The width 440 can be a selected width such as about 4-5 cm, including about 3 cm. Additionally, the width 440 can allow for a wide area of connection of soft tissue. Further, the width can be carried throughout a dimension, such as a length 450 of the soft tissue connection portion 436. Additionally, a soft tissue immobilization system 451 can include a washer 452 and/or screw or bolt (not illustrated here) connections that can be provided for initial immobilization of soft tissue relative to the soft tissue connection portion 436. As discussed herein, the soft tissue immobilization system can be positioned inferiorly on the soft tissue connection portion 436. Additionally, the neck portion 332 can be interconnected with a stem 454 and the head portion 335 as discussed above. An exterior surface of the soft tissue connection portion of 436 can also define an arc having a radius, as discussed above. The arc can extend around a selected axis, such as the axis 337a of the neck 337. Alternatively, or in addition thereto, the radius may also be defined within the soft tissue connection portion of 436. Thus, the soft tissue connection portion of 436 can define a plurality of connection regions to create the substantially anatomical matching connections to mimic the natural facet connections of the femur as illustrated in FIG. 1.

With reference to FIG. 13, the soft tissue connection portion 536 can include a pinched or bulbous superior soft tissue connection region 538. The superior soft tissue connection region 538 can extend superiorly relative to the neck portion 332. The superior soft tissue connection region 538 can be provided to allow for connection of soft tissue relative to the soft tissue connection region 536. The bulbous superior connection portion 538 can include selected dimensions and be provided and formed for a connection of soft tissue relative to the soft tissue connection portion 536. The bulbous portion 536 can include a dimension, such as a portion of a circumference or surface of a selected dimension for soft tissue connection. The soft tissue connection portion 536 can also include a soft tissue immobilization system 539. The soft tissue immobilization system 539 can include a washer 540 and/or bolt or screw fixation (not illustrated in FIG. 13) portions similar to those discussed above. Again, as discussed herein, the soft tissue immobilization system 539 can be positioned inferiorly on the soft tissue connection portion 536.

An exterior surface of the soft tissue connection portion of 536 can also define an arc having a radius, as discussed above. The arc can extend around a selected axis, such as the axis 337a of the neck 337. Alternatively, or in addition thereto, the radius may also be defined within the soft tissue connection portion of 536. Thus, the soft tissue connection portion of 536 can define a plurality of connection regions to create the substantially anatomical matching connections to mimic the natural facet connections of the femur as illustrated in FIG. 1. Additionally, the neck portion 332 can be connected with a stem portion 544 and the head 335.

It is understood that the soft tissue connection portion, according to the various embodiments as discussed herein, can include a porous surface for soft tissue ingrowth. The porous surface for soft tissue ingrowth can include a porous coating on a substantially solid or non-porous substrate, such as a titanium or stainless steel substrate. Alternatively, or in addition thereto, the porous surface can include a porous construct, such as Regenerex® porous metal sold by Biomet, Inc. or additively manufactured constructs. either alone and/or to be fixed to a substrate. As a further alternative to the soft tissue connection portion can be formed entirely of a porous metal such as the Regenerex® porous metal or additively manufactured constructs, and be interconnected with the neck portion, according to the various embodiments.

According to the various embodiments, the disclosed prostheses as illustrated in FIGS. 2-14 include various embodiments of soft tissue connection regions 38, 238, 360a, 360b, 438, and 538 that may or may not be used together or formed together in one construct. The soft tissue connection regions can generally include porous coated constructs and/or porous metal constructs. Moreover, according to various embodiments, that may or may not be combined, soft tissue immobilization systems 46, 46a, 46b, 253, 363a-363b, 451, and 539 can be positioned substantially inferior relative to respective soft tissue connection portions and/or the anatomy into which they are placed, as discussed above. This inferior placement, according the various embodiments described herein, allows for a large, including a greatest amount, of uninterrupted contact surface area between the soft tissue and the soft tissue connection regions, according to various embodiments.

Additionally, it is understood that the soft tissue connection portions can be interconnected with the neck portions according to the various embodiments. Accordingly, it is understood that the variations and various embodiments disclosed herein can be combined in appropriate manners, such as those understood by ones skilled in the art, can provide a selection of configurations for use by a selected user. Thus, it is understood, that the specific embodiments treated herein are not understood to limit the various combinations that further selected soft tissue connection portions.

Figure 14:
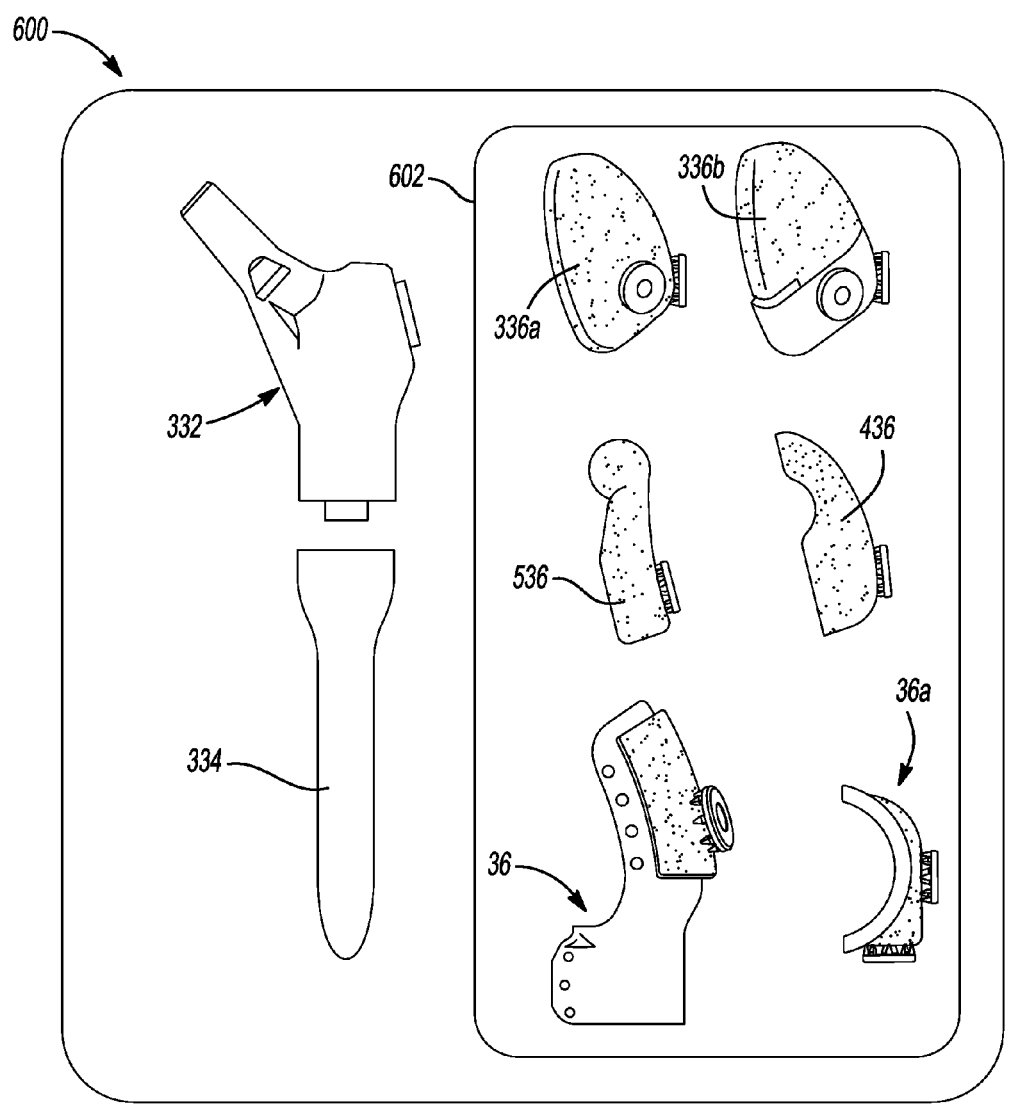
FIG. 14 is a view of a kit of a femoral prosthesis with a plurality of soft tissue connection portions.

Additionally, it is understood that a kit 600, as illustrated in FIG. 14, can be provided to include at least one neck portion such as the dovetail neck connection portion 332, the stem portion 334, and a plurality of soft tissue connection portions 602. The plurality of soft tissue connection portions 602 can include all those illustrated above for connection with the selected neck portion, such as the neck portion 332. It will be understood that any selected configuration of soft tissue connection portion can be provided and selected by a user. The plurality of soft tissue connection portions 602 can each include different sizes, shapes, and configurations to allow intraoperative selection by a user.

Accordingly, the kit 600 can be provided to a user for use during a procedure. As discussed above, an intraoperative decision can be made, such as after making an incision in the patient, to select whether or not a soft tissue connection is necessary and, then, a selection from the various plurality of soft tissue connection portions 602 from the kit 600 can be made to provide for a selected and patient-specific or an appropriate connection or configuration. Thus, it is understood that the soft tissue connection portions 602 provided in the kit 600 can be selected intraoperatively by a user for providing an appropriate prosthesis to a patient. The prosthesis can be substantially patient specific, although not initially designed based upon data, such has image data, of the patient. It is understood, however, that patient data can be used to form a soft tissue connection portion that can be one of at least a plurality of soft tissue connection portions provided in the kit 600 or as an augment to the kit 600 for selection by a user.

Generally, the femur 20 can be prepared as is generally understood by one skilled in the art. For example, an incision can be made and the user can inspect the subject. A proper resection can then be made and the user can again inspect the subject. Based on the inspection an evaluation and determination can be made as to a select which, if any, of the plurality of soft tissue connections portions, such as the soft tissue connection portions 602, can or should be interconnected with a selected one of the neck portion. Again, it is understood, that based on the determination that no soft tissue connection portion need be selected. Additionally, a set of instructions can be executed by a processor to determine which soft tissue connection portion would be proper for a specific subject. The instructions can include inputs for amount of tissue resected, age of the subject, condition of the soft tissue, and other proper inputs. Once selected, the soft tissue connection portion can be connected with the neck portion. The connected soft tissue connection portion and the neck portion can then be connected to a stem either prior to or after implantation of the stem. The procedure can then be completed as understood by one skilled in the art.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of implanting a prosthesis in a proximal femur, comprising:
   forming an incision in a patient;
   evaluating a patient and resecting a proximal femur;
   selecting a prosthesis including a connection for a soft tissue connection portion;
   after forming the incision, determining whether a soft tissue connection portion is to be connected to the prosthesis;
   if it is determined that a soft tissue connection portion is to be connected to the prosthesis, selecting and connecting the soft tissue connection portion; and
   implanting the prosthesis into the patient;
   wherein the connection for the soft tissue connection portion includes at least two connection portions at two different locations including an anterior facet (AF), a lateral facet (LF), a posterior facet (PF), or a superior posterior facet (SPF).

2. The method of claim 1, wherein the soft tissue connection portion is connected to the prosthesis, further comprising:
   connecting a soft tissue of the patient to the connected soft tissue connection portion.

3. The method of claim 2, wherein connecting the soft tissue includes connecting with a locking member the soft tissue to a first soft tissue connection region of the soft tissue connection portion to immobilize a portion of the soft tissue to the soft tissue connection portion.

4. The method of claim 3, further comprising;
   frictionally holding the soft tissue to the soft tissue connection portion with a porous portion at a second soft tissue connection region of the soft tissue connection portion.

5. The method of claim 4, wherein connecting with the locking member includes:
   clamping between the first soft tissue connection region and a washer a portion of soft tissue to be immobilized; and
   passing a screw through the washer to engage the soft tissue connection portion.

6. The method of claim 5, wherein frictionally holding the soft tissue to the second soft tissue connection region occurs a distance from a location of the first soft tissue connection region.

7. The method of claim 2, further comprising:
   selecting on the selected soft tissue connection portion at least a first soft tissue connection region and a second soft tissue connection region spaced apart from the first soft tissue connection region;
   wherein connecting the soft tissue of the patient to the connected soft tissue connection portion includes connecting a first portion of the soft tissue to the first region and connecting a second portion of the soft tissue to the second region.

8. A method of implanting a prosthesis in a proximal femur, comprising:
   forming an incision in a patient;
   evaluating a patient and resecting a proximal femur;
   selecting a prosthesis including a connection for a soft tissue connection portion;
   after forming the incision, determining whether a soft tissue connection portion is to be connected to the prosthesis;
   if it is determined that a soft tissue connection portion is to be connected to the prosthesis, selecting and connecting the soft tissue connection portion; and
   implanting the prosthesis into the patient;
   wherein selecting the prosthesis including the connection for the soft tissue connection portion includes connecting the soft tissue connection portion that includes at least two of an anterior facet (AF), a lateral facet (LF), a posterior facet (PF), or a superior posterior facet (SPF);
   selecting at least a first soft tissue connection region and a second soft tissue connection region spaced apart from the first soft tissue connection region includes selecting for the first soft tissue connection region one of the anterior facet (AF), the lateral facet (LF), the posterior facet (PF), or the superior posterior facet (SPF) and selecting for the second soft tissue connection region a different one of the anterior facet (AF), the lateral facet (LF), the posterior facet (PF), or the superior posterior facet (SPF).

9. A system of a prosthesis to replace a proximal femoral portion, comprising:
   a stem portion;
   a neck portion including a head connection region;
   a soft tissue connection mechanism formed by at least a portion of the neck portion including a male taper extending away from the head connection region; and
   a soft tissue connection portion defining a female taper to engage the male taper and having at least a first tissue connection surface spaced separate and spaced superiorly from a second tissue connection surface;

wherein the first tissue connection surface is configured to engage a first soft tissue portion and the second tissue connection surface is configured to engage a second soft tissue portion spaced apart from the first tissue connection surface;

wherein the first surface and the second surface are substantially planar and meet at a raised region.

10. The system of claim 9, further comprising:
a modular soft tissue connection portion configured to be connected to the soft tissue connection portion.

11. The system of claim 9, wherein the stem portion and the neck portion are configured to be connected and implanted in an absence of the soft tissue connection portion.

12. A system of a prosthesis to replace a proximal femoral portion, comprising:
a stem portion;
a neck portion including a head connection region;
a soft tissue connection mechanism formed by at least a portion of the neck portion including a male taper extending away from the head connection region; and
a soft tissue connection portion defining a female taper to engage the male taper and having at least a first tissue connection surface spaced separate and spaced superiorly from a second tissue connection surface;
wherein the first tissue connection surface is configured to engage a first soft tissue portion and the second tissue connection surface is configured to engage a second soft tissue portion spaced apart from the first tissue connection surface;
wherein the first surface is a first portion of a curve of the soft tissue connection portion and the second surface is a second portion of the curve of the soft tissue connection portion;
wherein the soft tissue connection portion extends superiorly of the head connection region.

13. A system of a prosthesis to replace a proximal femoral portion, comprising:
a stem portion;
a neck portion including a head connection region;
a soft tissue connection mechanism formed by at least a portion of the neck portion including a male taper extending away from the head connection region; and
a soft tissue connection portion defining a female taper to engage the male taper and having at least a first tissue connection region spaced apart from a second tissue connection region;
a washer fixation system to immobilize soft tissue to the first region;
wherein the second region includes a porous surface to frictionally engage the soft tissue.

14. A system of a prosthesis to replace a proximal femoral portion, comprising:
a stem portion;
a neck portion including a head connection region;
a soft tissue connection mechanism formed by at least a portion of a lateral region of the neck portion including one of a tapered rail, wherein the tapered rail has a dovetail shape and includes an edge that tapers outwardly from a central axis of the tapered rail, or a groove;
a soft tissue connection portion defining the other of the tapered rail or the groove that engages the tapered rail to fix the soft tissue connection portion of the soft tissue connection mechanism; and
a soft tissue immobilization system including a screw operable to provide at least initial fixation of a soft tissue to the soft tissue connection portion;

wherein the soft tissue connection portion includes at least a first surface for connection of soft tissue formed at an angle relative to a second surface for connection of soft tissue.

15. The system of claim 14, wherein the first region and the second region are substantially planar.

16. The system of claim 15, wherein the first region is a first portion of a curve of the soft tissue connection portion and the second region is a second portion of the curve of the soft tissue connection portion.

17. The system of claim 14, wherein the soft tissue connection portion extends superiorly of the head connection region.

18. The system of claim 14, further comprising:
a modular soft tissue connection portion configured to be connected to the soft tissue connection portion.

19. The system of claim 14, wherein the stem portion and the neck portion are configured to be connected and implanted in an absence of the soft tissue connection portion.

20. The system of claim 14, wherein the soft tissue connection portion extends from a first end to a second end, wherein the first end includes a bulbous region.

21. A kit for a system of a prosthesis to replace a proximal femoral portion, comprising:
a stem portion;
a neck portion including a head connection region and a male taper;
a soft tissue connection mechanism formed by at least a portion of the neck portion; and
a plurality of soft tissue connection portions, wherein each of the plurality of soft tissue connection portions include an external surface having a dimension different from each other external surface and each external surface of the plurality of soft tissue connection portions has a shape of the external surface different from the other external surface of the soft tissue connection portions;
wherein each external surface forms a region to frictionally engage and hold soft tissue;
wherein each of the plurality of soft tissue connection portions includes a female taper to engage the male taper.

22. The kit of claim 21, wherein the neck portion includes a soft tissue connection mechanism formed by at least a portion of the neck portion including a tapered rail extending from a surface of the neck portion, wherein the tapered rail includes an edge that tapers outwardly from a central axis of the tapered rail;
wherein each of the plurality of soft tissue connection portions includes a groove to engage the tapered rail to fix the soft tissue connection portion of the soft tissue connection mechanism;
wherein each of the plurality of the soft tissue connection portion includes at least a first region for connection of soft tissue offset at an angle relative to a second region for connection of soft tissue.

23. The kit of claim 22, wherein in each of the plurality of soft tissue connection portions the first region is at least one of a different size or spaced a different distance from the second region.

24. The kit of claim 21, wherein each of the plurality of the soft tissue connection portion includes at least a first region for connection of soft tissue offset at a different angle relative to a second region for connection of soft tissue.

25. A kit for a system of a prosthesis to replace a proximal femoral portion, comprising:
a stem portion;
a neck portion including a head connection region;

a soft tissue connection mechanism formed by at least a portion of the neck portion;
a plurality of soft tissue connection portions, wherein each of the plurality of soft tissue connection portions include an external surface having a dimension different from each other external surface and each external surface of the plurality of soft tissue connection portions has a shape of the external surface different from the other external surface of the soft tissue connection portions; and
a washer fixation system to immobilize soft tissue to each of the soft tissue connection portions on the external surface;
wherein each external surface forms a region to frictionally engage and hold soft tissue;
wherein the external surface includes a porous surface.

* * * * *

UNITED STATES PATENT AND TRADEMARK OFFICE
CERTIFICATE OF CORRECTION

| | | |
|---|---|---|
| PATENT NO. | : 8,979,940 B2 | Page 1 of 1 |
| APPLICATION NO. | : 13/714570 | |
| DATED | : March 17, 2015 | |
| INVENTOR(S) | : Porter et al. | |

It is certified that error appears in the above-identified patent and that said Letters Patent is hereby corrected as shown below:

On page 2, in column 2, References cited under "Other Publications", line 1, delete "Orthopaedic" and insert --Orthopedic--, therefor In the claims In column 14, line 4, in Claim 4, delete "comprising;" and insert --comprising:--, therefor Signed and Sealed this
Tenth Day of November, 2015

Michelle K. Lee
*Director of the United States Patent and Trademark Office*